Dec. 10, 1957 S. D. McGREDY IV Plant Pat. 1,667
ROSE PLANT
Filed Jan. 23, 1957
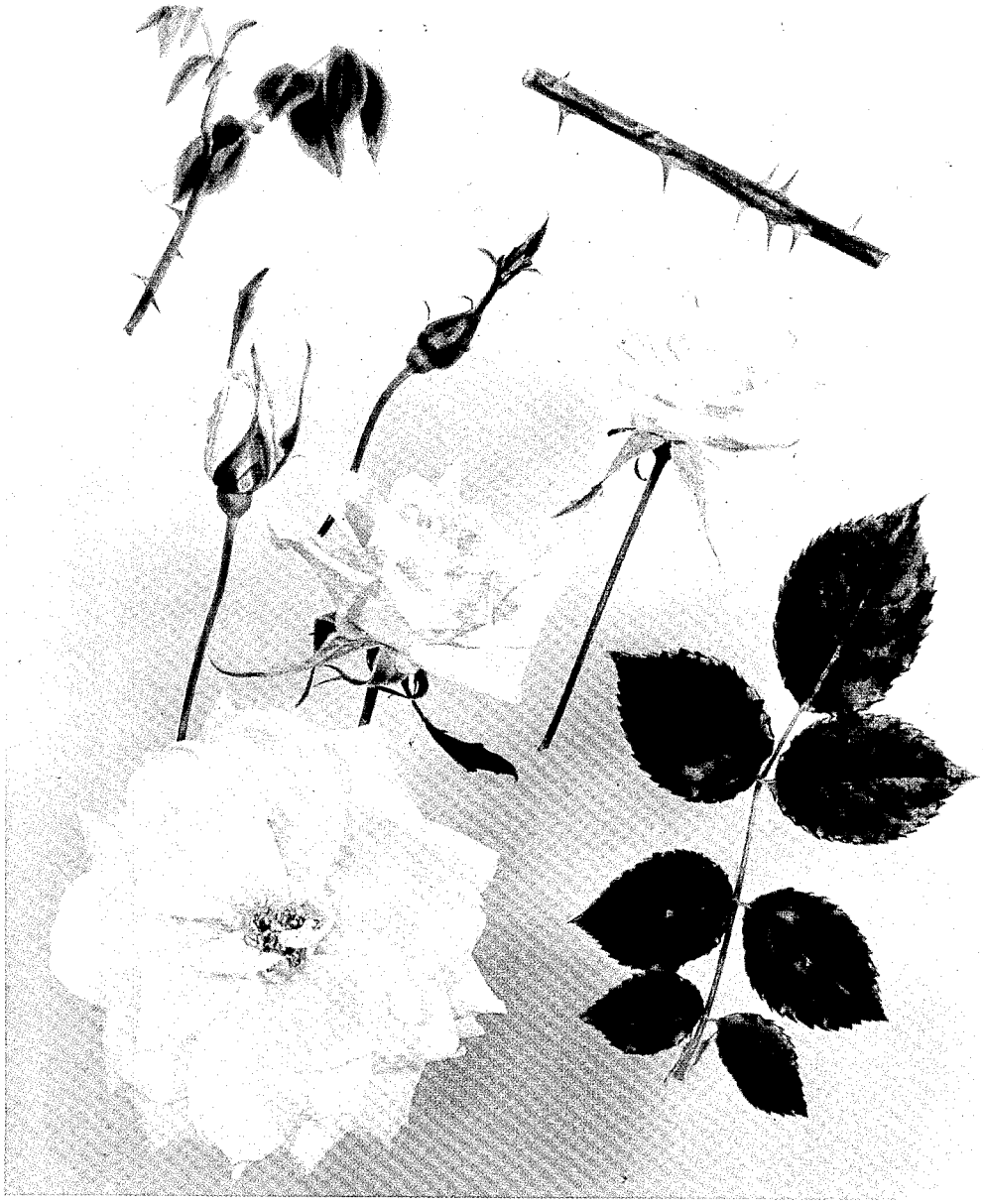
Inventor.
S. D. McGredy IV
By: Robert Robb
Attorneys.

United States Patent Office

Plant Pat. 1,667
Patented Dec. 10, 1957

1,667

ROSE PLANT

Samuel D. McGredy IV, Portadown, Ireland, assignor to Jackson & Perkins Company, Newark, N. Y., a corporation of New York Application January 28, 1957, Serial No. 636,845

1 Claim. (Cl. 47—61)

The present invention relates to a new and distinct variety of rose plant of the large-flowered polyantha class, which was originated by me by crossing the variety "Poulsen's Yellow" (unpatented) with an unnamed and unpatented seedling.

The primary objective of this breeding was to produce a new rose variety of the floribunda class, but which bears deeper colored flowers than those of the parent variety "Poulsen's Yellow." This objective was fully achieved, along with other improvements, as evidenced by the following characteristics which are outstanding in the new variety:

(1) The very rich, glossy, Forest-Green foliage;

(2) The new rich color of the flowers which have a general color tonality of Light Cadmium, faintly overcast with Deep Chrome;

(3) The distinctive color of the flower anthers which have a general color tonality of Maize Yellow, outlined with Garnet Brown;

(4) The extreme floriferousness of the plant; and (5) The long-lasting quality of the flowers as cut flowers.

Asexual reproduction of my new variety by budding, as performed at Newark, New York, U. S. A., and also at Pleasanton, California, U. S. A., shows that the aforementioned characteristics come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"Poulsen's Yellow."
*Pollen parent.*—An unnamed seedling.

Classification:
*Botanic.*—Large-flowered polyantha.
*Commercial.*—Floribunda.

*Flower*

(Observations made from specimens grown in a greenhouse at Newark, New York, U. S. A., in the early morning near the middle of July.)

Blooming habit: Recurrent—Continuous.

Bud:
*Size.*—Medium.
*Form.*—Pointed; ovoid; is not affected by wet or hot weather.
*Color.*—When sepals first divide—Peach Red, Plate 1. When petals begin to unfurl—Deep Chrome, Plate 3. When half-blown: inside of petals—Light Orange-Yellow, Plate 3, lightly overcast with Light Cadmium, Plate 4; reverse of petals—Deep Chrome, Plate 3, with outer edges lightly overcast with Mikado Orange, Plate 3.
*Sepals.*—Slightly branched; with "hood" above bud; curl back when petals begin to unfurl. Color: inside—Turtle Green, Plate 32; outside—Light Bice Green, Plate 17.
*Calyx.*—Color—Parrot Green, Plate 6. Shape—pear. Size—small. Aspect—smooth. Odor when rubbed—none.
*Peduncle.*—Length — medium. Aspect — smooth. Strength—erect; slender. Color—Rainette Green, Plate 31.
*Opening.*—Opens up well; is not affected by adverse weather conditions.

Bloom:
*Size.*—Medium. Average size when fully expanded—3½ inches.
*Borne.*—Several together and in irregular clusters.
*Stems.*—Medium length; normal strength.
*Form (when first open).*—Flat. Permanence—retains its form to the end.
*Petalage.*—Double (full but open center). Number of petals under normal conditions—from 45 to 50.
*Color.*—Center of flower—Deep Chrome, Plate 3. Outer petals—Light Orange-Yellow, Plate 3, lightly overcast with Capucine Orange, Plate 3. Base of petals (aiglet)—Lemon Yellow, Plate 4. Inside of petals—Light Cadmium, Plate 4, faintly overcast with Deep Chrome, Plate 3. Reverse of petals—Buff-Yellow, Plate 4, lightly overcast with Empire Yellow, Plate 4, at the lower half of the petal. General tonality from a distance—Light Cadmium, Plate 4.
*Discoloration.*—General tonality at end of first day—Light Cadmium, Plate 4, overcast with Deep Chrome, Plate 3. Second day—Light Cadmium, Plate 4, lightly overcast with Deep Chrome, Plate 3. Third Day—Light Orange-Yellow, Plate 3.

Petals:
*Texture.*—Leathery; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Few; small.
*Persistence.*—Drop off cleanly.
*Fragrance.*—Strong. Nature—fruity (russet apple).
*Lasting quality.*—On the plant—very long. As cut flower—very long.

*Genital organs*

Stamens, anthers: Small; many; regularly arranged around styles. Color—Maize Yellow, Plate 4, outlined with Garnet Brown, Plate 1.
Stamens, filaments (threads): Medium length. Color—Spectrum Red, Plate 1.
Pollen: Color—Baryta Yellow, Plate 4.
Styles: Bunched; uneven length; medium length; thin.
Stigmas: Color—Straw Yellow, Plate 16.
Ovaries: All enclosed in calyx.
Hips: None.
Seeds: None.

*Plant*

Form: Bush.
Growth: Vigorous; upright.
Foliage: Compound of 5 to 7 leaflets.
*Size.*—Large.
*Quantity.*—Normal.
*Color.*—New foliage: upper side—Lettuce Green, Plate 5, with edges of leaf Garnet Brown, Plate 1;

under side—Yellowish Oil Green, Plate 5, lightly overcast with Garnet Brown, Plate 1. Old foliage: upper side—Forest Green, Plate 17; under side—Biscay Green, Plate 17.

*Shape.*—Oval pointed.

*Texture.*—Upper side—leathery; glossy. Under side—smooth.

*Ribs and veins.*—Ordinary.

*Edge.*—Serrated (saw-toothed).

*Serration.*—Both double and single; sharp.

*Leaf stem.*—Color—Absinthe Green, Plate 31. Under side—prickly.

*Stipules.*—Medium length; smooth.

Wood:

*New wood.*—Color—Lettuce Green, Plate 5. Bark—smooth.

*Old wood.*—Color—Biscay Green, Plate 17. Bark—smooth.

Thorns:

*Thorns.*—Quantity: on main stalks from base—ordinary; on laterals from stalk—ordinary. Form— narrow base; medium length; hooked downward. Color (when young)—Spinel Red, Plate 26. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by its very rich, glossy, Forest Green foliage, the rich color of its flowers which have a general color tonality of Light Cadmium faintly overcast with Deep Chrome, the distinctive color of the flower anthers which have a general color tonality of Maize Yellow outlined with Garnet Brown, the extreme floriferousness of the plant, and the long-lasting quality of the flowers as cut flowers.

No references cited.